United States Patent
Ferguson

(10) Patent No.: US 7,641,158 B2
(45) Date of Patent: Jan. 5, 2010

(54) INTRAVENOUS STAND

(75) Inventor: Kevin Mark Ferguson, Middletown, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 36 days.

(21) Appl. No.: 11/823,106

(22) Filed: Jun. 26, 2007

(65) Prior Publication Data

US 2008/0035804 A1 Feb. 14, 2008

Related U.S. Application Data

(60) Provisional application No. 60/816,657, filed on Jun. 27, 2006.

(51) Int. Cl.
*F16M 11/00* (2006.01)
(52) U.S. Cl. ............... 248/157; 248/129; 248/910
(58) Field of Classification Search ........... 248/157, 248/129, 163.1, 910; 606/34, 241; 5/503.1, 5/658; 280/47.35, 79.3; 211/187; 108/50.02
See application file for complete search history.

(56) References Cited

U.S. PATENT DOCUMENTS

| | | | | |
|---|---|---|---|---|
| 1,374,633 | A * | 4/1921 | Boyle | 108/106 |
| 3,410,268 | A * | 11/1968 | Lencci | 604/31 |
| 3,830,170 | A * | 8/1974 | Faulstich | 108/162 |
| 4,332,378 | A | 6/1982 | Pryor | |
| 4,572,594 | A * | 2/1986 | Schwartz | 312/209 |
| 4,706,368 | A * | 11/1987 | Crissman et al. | 29/525.09 |
| 4,832,294 | A * | 5/1989 | Eidem | 248/125.8 |
| 5,000,407 | A * | 3/1991 | Juji et al. | 248/125.8 |
| 5,069,570 | A | 12/1991 | Pryor et al. | |
| D325,137 | S * | 4/1992 | Porter | D6/479 |
| 5,110,076 | A * | 5/1992 | Snyder et al. | 248/125.3 |
| 5,114,023 | A * | 5/1992 | Lavin | 211/107 |
| 5,125,607 | A | 6/1992 | Pryor | |
| 5,137,237 | A | 8/1992 | Haskins | |
| 5,337,992 | A | 8/1994 | Pryor et al. | |
| 5,344,169 | A | 9/1994 | Pryor et al. | |
| 5,354,031 | A * | 10/1994 | Bilotti | 248/519 |
| 5,372,265 | A * | 12/1994 | Monch | 211/187 |
| 5,553,707 | A * | 9/1996 | Lion | 206/315.9 |
| 5,556,065 | A * | 9/1996 | Wadley | 248/129 |
| 5,828,502 | A * | 10/1998 | Afshari | 359/819 |
| 5,857,685 | A * | 1/1999 | Phillips et al. | 280/47.35 |
| 5,890,687 | A * | 4/1999 | Pryor et al. | 248/158 |
| D431,936 | S * | 10/2000 | Moen et al. | D6/461 |
| 6,293,506 | B1 * | 9/2001 | Gutgsell et al. | 248/188.1 |

OTHER PUBLICATIONS

Unknown, IV Stands, Pryor Products Online Catalog, Pryor Products, Inc., Oceanside, CA, USA, [date unknown but prior to Jun. 26, 2007].

* cited by examiner

*Primary Examiner*—Korie Chan
(74) *Attorney, Agent, or Firm*—Taft Stettinius & Hollister, LLP

(57) ABSTRACT

A portable intravenous stand comprising: (a) a base including a plurality of wheels; (b) a plurality of vertical supports extending from the base; (c) a plurality of cross-members mounted to the plurality of vertical supports to maintain the vertical supports in relative position to one another; and (d) an intravenous retainer loop mounted to at least one of the plurality of vertical supports.

13 Claims, 6 Drawing Sheets

INTRAVENOUS STAND

CROSS REFERENCE TO RELATED APPLICATIONS

The present application claims the benefit under 35 U.S.C. §119 to U.S. Provisional Patent Application Ser. No. 60/816,657, filed Jun. 27, 2006 and titled "TRI-POLE I.V. STAND," the disclosure of which is hereby incorporated by reference.

INTRODUCTION TO THE INVENTION

Field of the Invention

The present invention is directed to devices used as mobile support stands for intravenous ("I.V.") fluid containers, pumps, monitors and other equipment. The exemplary embodiments described herein accommodate a greater number of pieces of equipment, with a smaller footprint, and with the same or better stability than prior mobile support stands.

It is a first aspect of the present invention to provide a portable intravenous stand comprising: (a) a base including a plurality of wheels; (b) a plurality of vertical supports extending from the base; (c) a plurality of cross-members mounted to the plurality of vertical supports to maintain the vertical supports in relative position to one another; and (d) an intravenous retainer loop mounted to at least one of the plurality of vertical supports.

In a more detailed embodiment of the first aspect, at least one of the plurality of cross-members includes an opening therethrough. In yet another more detailed embodiment, the plurality of vertical supports are uniformly distributed about a vertical axis extending through the base. In a further detailed embodiment, the base includes at least three symmetrical legs, and at least three of the symmetrical legs each include at least one of the plurality of wheels. In still a further detailed embodiment, the invention also includes supplemental weights mounted to the base. In a more detailed embodiment, the invention also includes a handle mounted to at least one of a vertical support of the plurality of vertical supports and a cross-member of the plurality of cross-members. In a more detailed embodiment, the invention also includes a plurality of intravenous retainer loops mounted to at least one of the plurality of vertical supports and the plurality of cross-members. In another more detailed embodiment, the invention also includes a plurality of clamps vertically repositionable along at least one of the plurality of vertical supports. In yet another more detailed embodiment, at least one of the plurality of supports is circular in cross-section.

It is a second aspect of the present invention to provide a portable intravenous stand comprising: (a) a portable base; (b) a plurality of vertical supports mounted to the portable base, the plurality of vertical supports including at least three supports triangularly oriented; (c) a plurality of platforms mounted to the plurality of vertical supports, at least one of the plurality of platforms mounted to the at least three supports to maintain the at least three supports in a triangular orientation; and (d) an intravenous retainer loop mounted to at least one of the plurality of vertical supports.

In a more detailed embodiment of the second aspect, at least one of the plurality of platforms mounted to the at least three supports is vertically repositionable. In yet another more detailed embodiment, the invention also includes a supplemental weight mounted to the portable base, wherein the portable base includes a weight dowel receiving the supplemental weight. In a further detailed embodiment, the invention also includes a handle mounted to at least one of a vertical support of the plurality of vertical supports and a platform of the plurality of platforms. In still a further detailed embodiment, the invention also includes a plurality of intravenous retainer loops mounted to at least one of a vertical support of the plurality of vertical supports and a platform of the plurality of platforms. In a more detailed embodiment, the portable base includes at least three symmetrical legs, and at least three of the symmetrical legs each include a wheel.

It is a third aspect of the present invention to provide a portable intravenous stand comprising: (a) a portable base; (b) a plurality of vertical supports mounted to the portable base, the plurality of vertical supports including at least three supports triangularly oriented; (c) a plurality of platforms repositionably mounted to the plurality of vertical supports, at least two of the plurality of platforms mounted to the at least three supports to maintain the at least three supports in a triangular orientation; (d) an intravenous loop mounted to at least one of: (i) the plurality of platforms, and (ii) the plurality of vertical supports; and (e) a plurality of repositionable clamps vertically repositionable along at least one of the plurality of vertical supports, where the portable base is disproportionately weighted to lower a center of gravity of the stand.

In a more detailed embodiment of the third aspect, the portable base includes a weight dowel receiving a supplemental weight to lower the center of gravity of the stand. In yet another more detailed embodiment, at least a portion of the portable base is generally circular in cross-section, and the portion of the portable base generally circular in cross-section includes a plurality of semicircular cut-outs distributed along the periphery of the cross-section.

DETAILED DESCRIPTION

The exemplary embodiments of the present invention are described and illustrated below to encompass devices used as mobile support stands for intravenous ("I.V.") fluid containers, pumps, monitors and other equipment. The exemplary embodiments described herein accommodate a greater number of pieces of equipment, with a smaller footprint, and with the same or better stability than prior mobile support stands. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
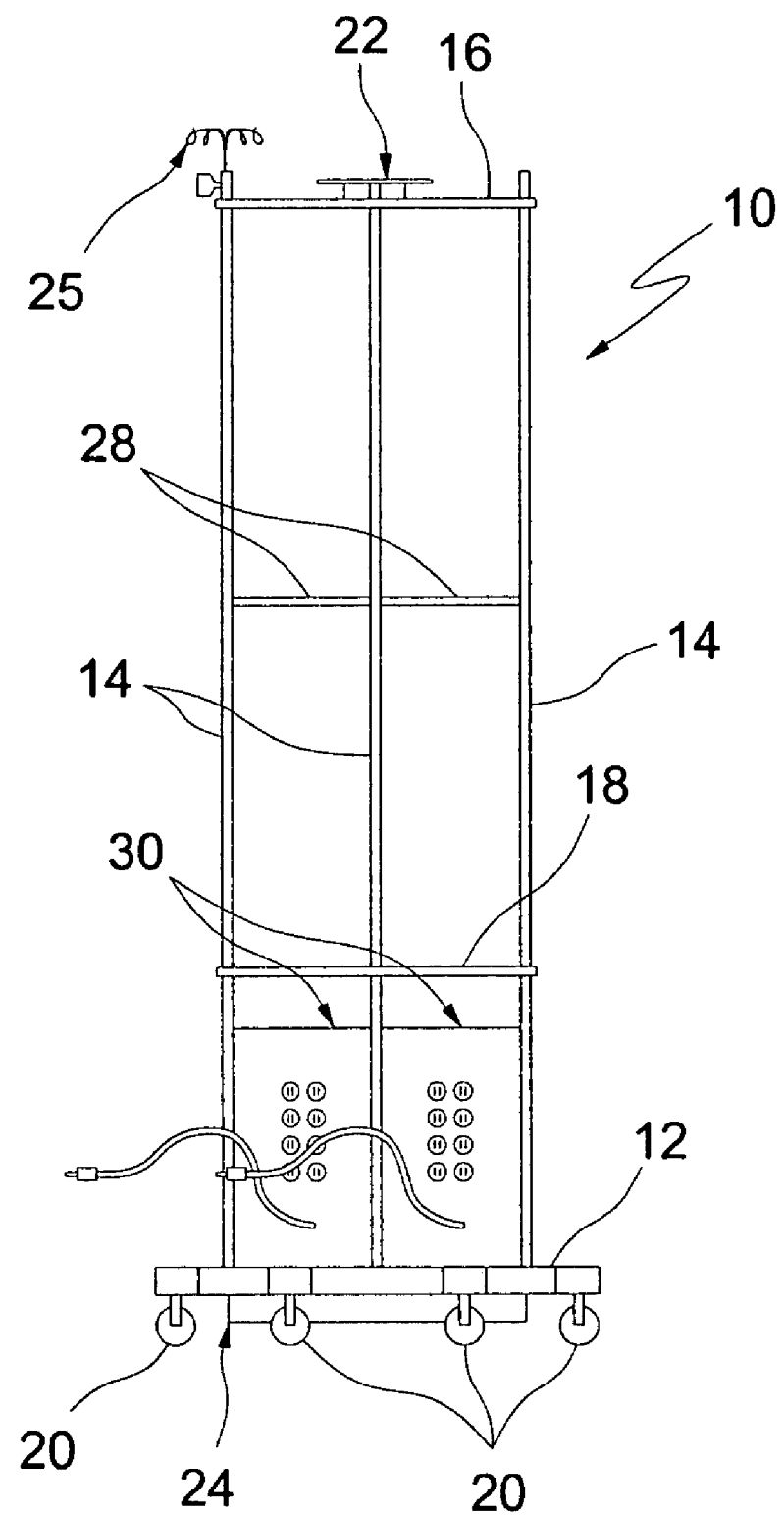
FIG. 1 is a plan view of a first exemplary intravenous stand pursuant to the instant invention.
Figure 2:
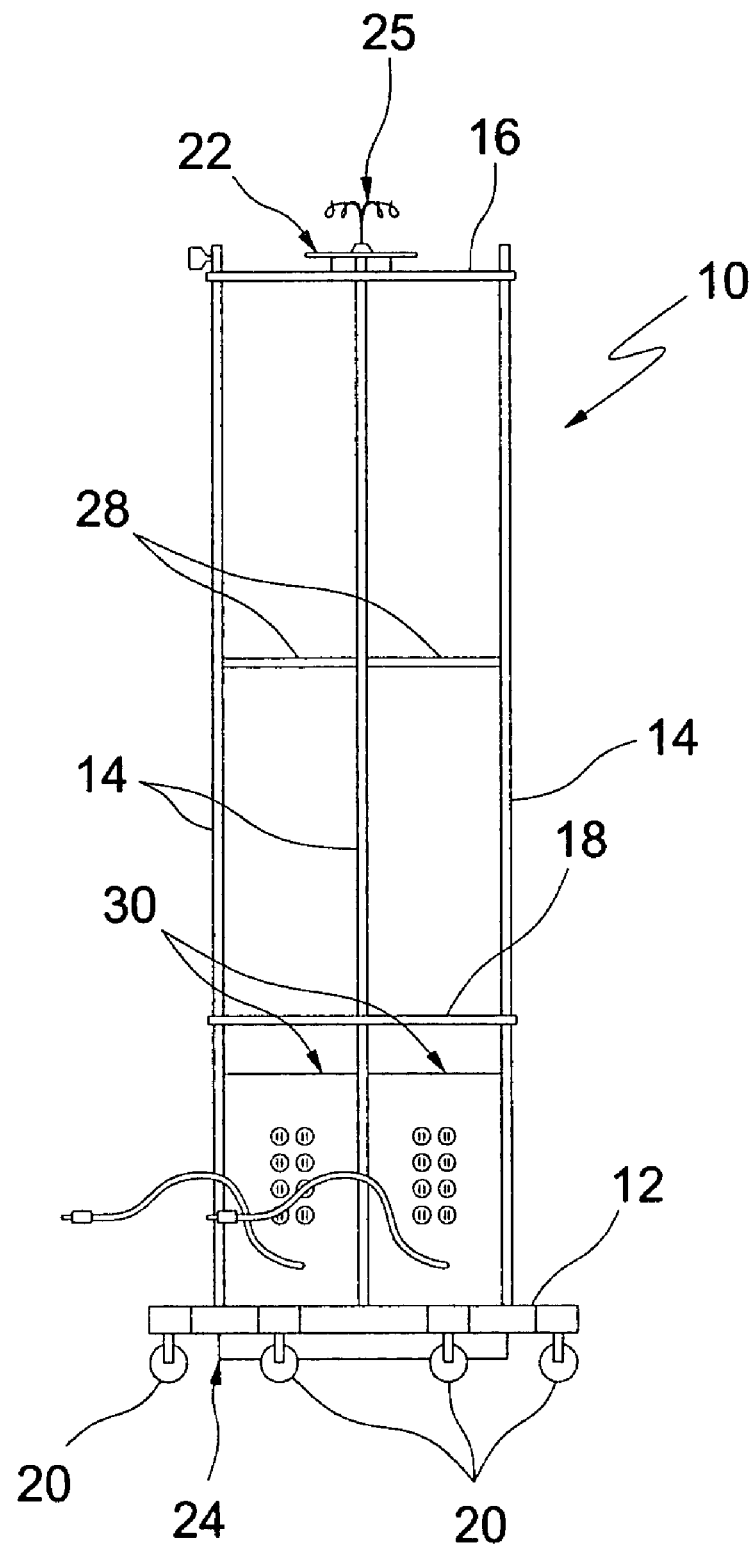
FIG. 2 is a plan view of the first exemplary intravenous stand rotated 120°.
Figure 3:
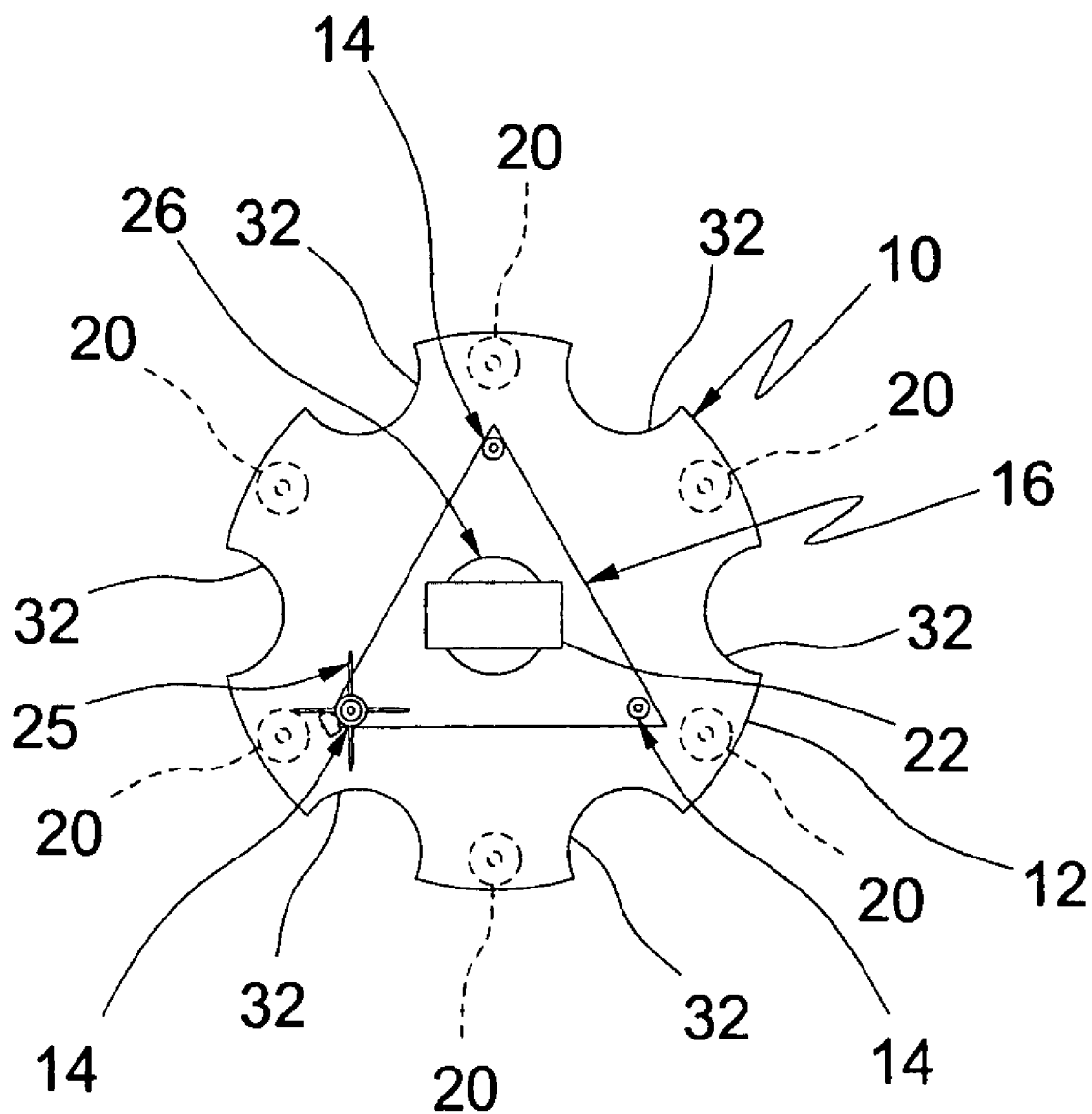
FIG. 3 is an overhead view of an exemplary tray for use with the first exemplary intravenous stand of FIGS. 1 and 2.

Referring to FIGS. 1-3, a first exemplary mobile intravenous stand 10 includes a base 12 with castered wheels 20, support poles 14, an upper platform 16, and an intermediate platform 18.

The base 12 is generally circular in shape with six generally semi-circular cut-outs 32. The base is supported from the floor by six castered wheels 20, one mounted to each of the six projections from the base. Additionally, a weight 24 is affixed to the underside of the base 12 (see FIGS. 1 and 2). The weight 24 is provided to assure that the center of gravity is approximate the base 12, even when the stand 10 is completely loaded with equipment.

The support poles 14 are hollow cylinders mounted orthogonally to the base 12 in a triangular arrangement. The support poles 14 are attached to the intermediate platform 18 and the upper platform 16 by way of set screws perpendicularly interfacing the poles 14 extending through holes approximate the apexes of the platforms. The intermediate platform 18 and upper platform 16 are generally triangular in shape and have openings 26 through their approximate centers to accommodate objects such as power cords or other throughputs. A standard equipment mount 22 is attached to the upper platform 16. A standard I.V. bag hanger 25 may be attached to the top of one or more of the support poles 14. Bars 28 are mounted horizontally between the support poles 14 at a height to allow for easy gripping as handles. Power supply units 30 are mounted on the support poles 14 between the base 12 and the intermediate platform 18.

In this first exemplary embodiment, the base 12 is 26 inches in diameter. The shape of the base 12 is designed to provide mounting locations for the castered wheels 20 that are widely spaced for increased stability while minimizing the overall weight of the mobile support stand. The weight 24 attached to the underside of the base 12 augments the stability of the stand by lowering its center of gravity. In exemplary form, the weight 24 is welded directly to the underside of the base 12, and is between 35 lbs and 45 lbs.

The total height of the mobile support stand 10 is approximately 68 inches. The support poles 14 are equally spaced 12 inches on center. The support poles 14 are hollow to minimize the overall weight of the stand as well as maintaining the center of gravity as low as possible. The support poles 14 have an outer diameter of 0.875 inches to accept standard medical equipment mounting hardware. The equilateral triangular arrangement of the support poles 14 in the exemplary embodiment provides an optimum number of poles 14 for mounting equipment and increases the stability of the stand by allowing an even distribution of weight. This first exemplary embodiment can support at least fifteen syringe pumps, one infusion pump, and one monitor, as well a numerous bags of I.V. fluid.

The handles 28 attached between the support poles 14 provide a convenient place to grasp the stand 10 when moving it.

The upper platform 16 and the intermediate platform 18 each have an opening 26 through which cables may be run. Cable management is important to prevent the inadvertent unplugging of equipment. Additionally, restraining the cables near the center of the stand reduces the risk of catching a cable on a protruding object when the stand is moved and reduces the trip hazard from loose cables.

The equipment mount 22 attached to the upper platform 16 provides a convenient location for various medical monitors. It is easily visible and reachable by the nursing staff. Including the monitor mount on the I.V. support stand eliminates the need for another rolling stand or other support equipment that would take up additional floor space and increase the difficulty of transporting a patient.

The support poles 14 extend from the base 12 generally to the full height of the stand 10. This design improves the strength and sturdiness of the stand and allows a greater number of pieces of equipment to be mounted safely. In addition, the weight of the supported equipment is directly transferred to the base 12, thereby eliminating unnecessary structural weak points that could be present in a design with branching support poles.

The power supplies 30 located on the lower portion of the support stand provide a convenient place to plug in the equipment that is mounted on the stand. By including on-board power supplies, fewer cords have to be unplugged when the stand is moved. Locating the power supplies near the bottom of the stand contributes to the low center of gravity and therefore increases the stability of the stand.

Although this first exemplary stand 10 shows only one I.V. bag hanger, each of the support poles is capable of receiving a hanger attachment. The I.V. bag hangers attached to support stands using thumbscrews.

Figure 4:
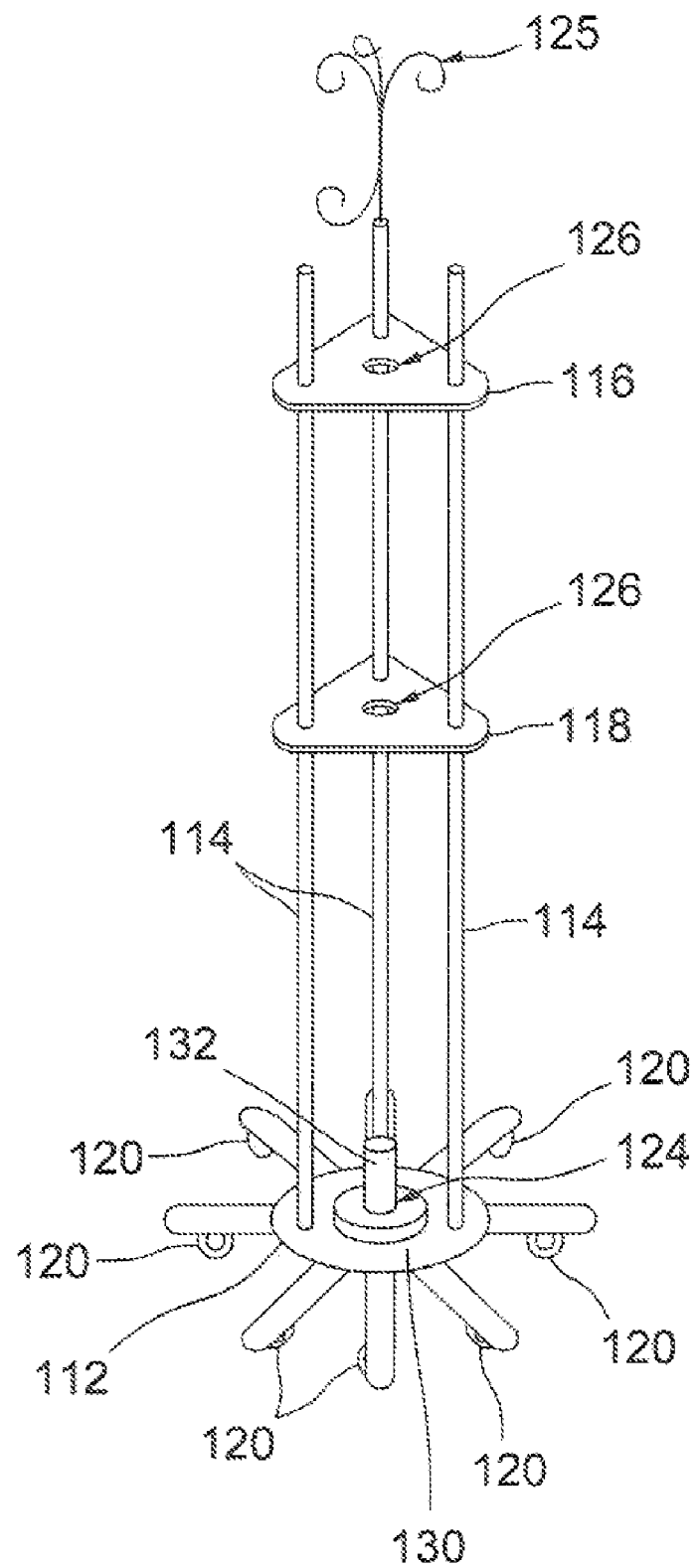
FIG. 4 is an elevated perspective view of a second exemplary intravenous stand.
Figure 5:
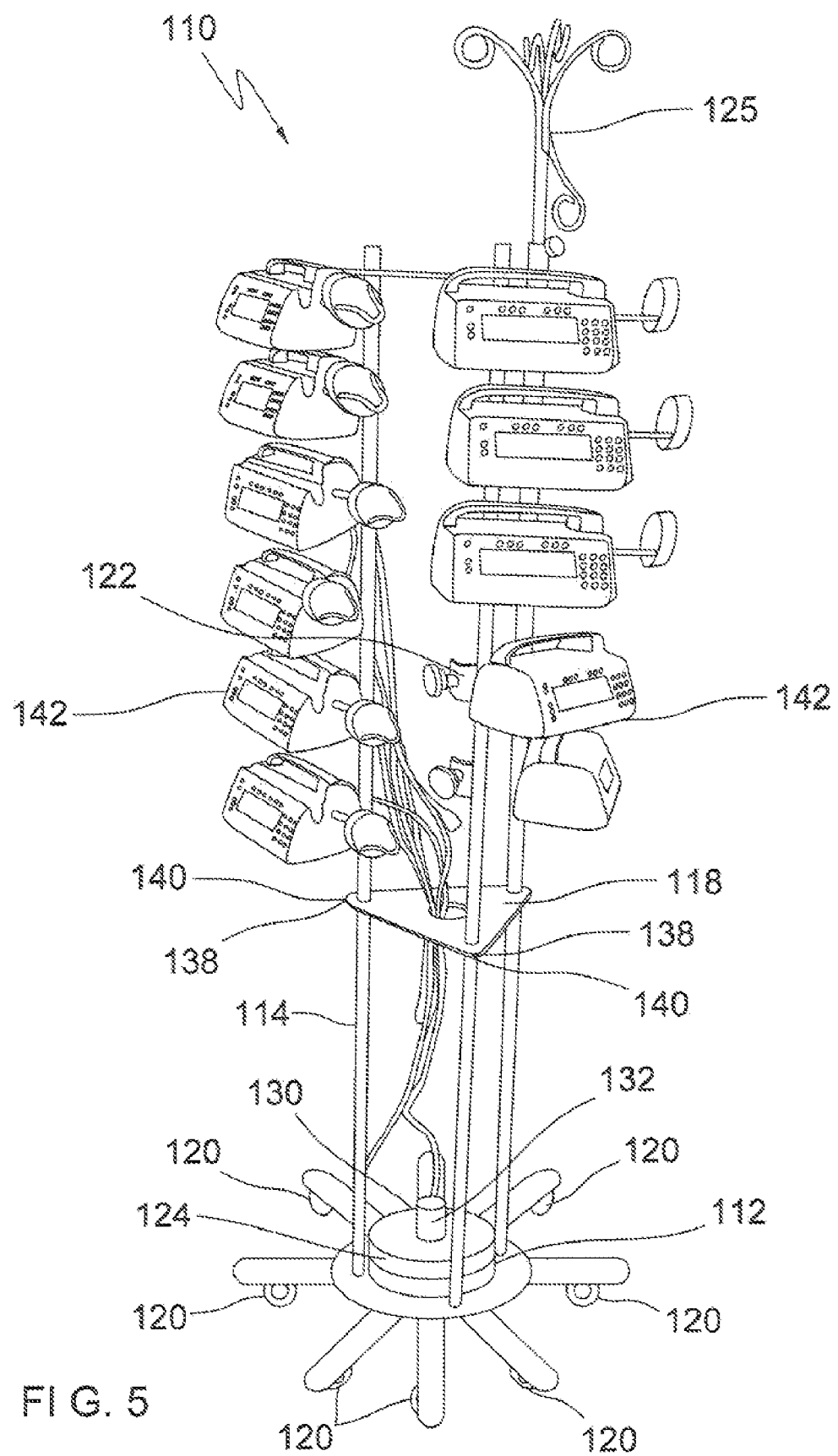
FIG. 5 is an elevated perspective view from the front of the second exemplary intravenous stand of FIG. 4, loaded with intravenous pumps.
Figure 6:
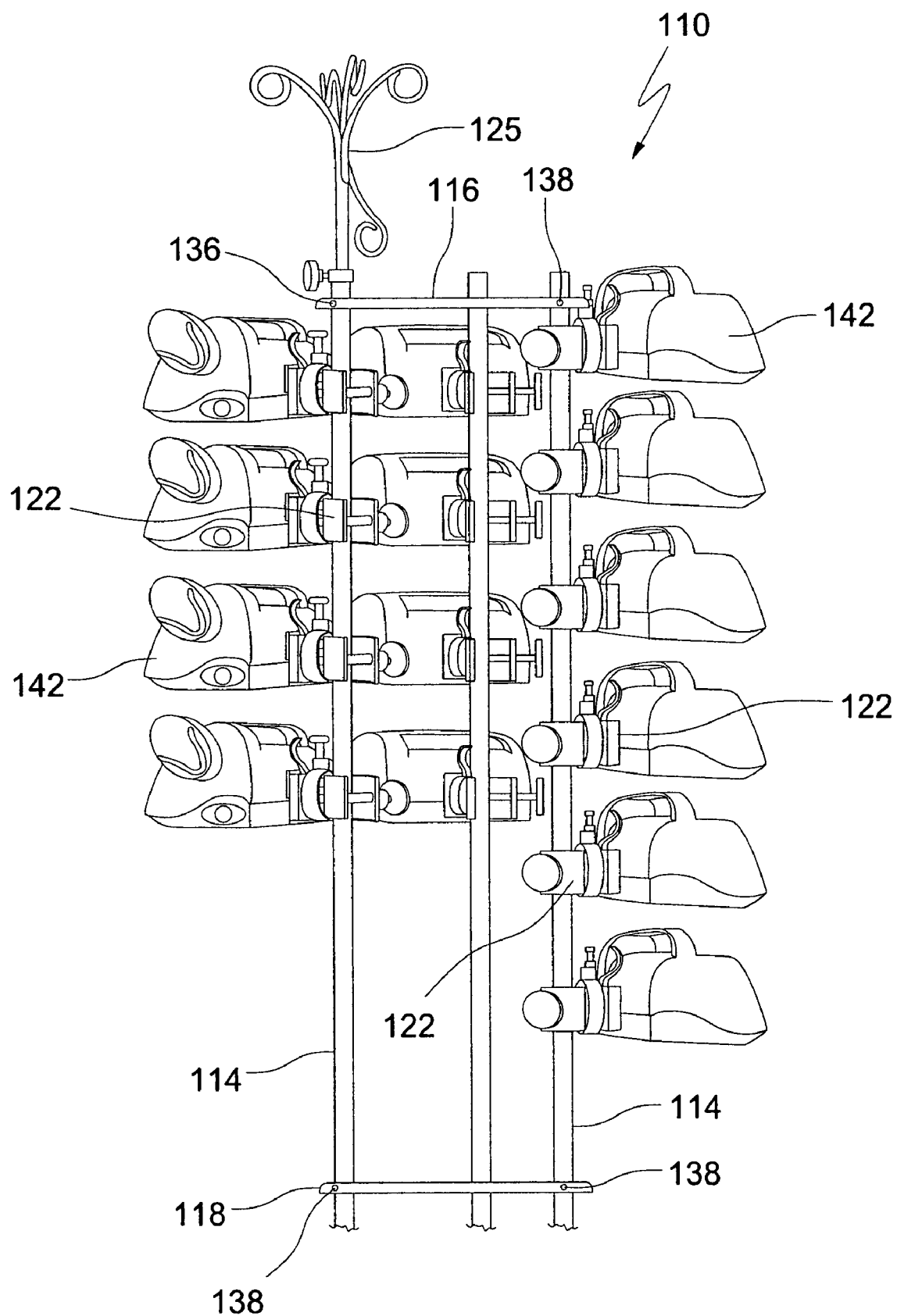
FIG. 6 is a profile view of a rear portion of the second exemplary intravenous stand of FIG. 4, loaded with intravenous pumps.

FIGS. 4-6 show a second exemplary I.V. stand 110. This second exemplary stand includes a base 112 with castered wheels 120, vertical support poles 114, an upper cross-member platform 116, and an intermediate cross-member platform 118. In this exemplary embodiment, the base 112 comprises eight uniformly distributed legs 128 and a central cross-member platform 130 that includes a weight retainer 132. The weight retainer 132 is adapted to receive the central cable passageway opening in circular or cylindrical supplemental weights 124 to lower the center of gravity of the stand 110. Each of the cross-member platforms 116, 118 includes a central opening 126, as well as secondary openings 136 approximate the apexes that allow throughput of each of the vertical support poles 114. In exemplary form, each cross-member platform 116, 118 includes a set screw opening 138 extending normal to the openings 136. Each set screw opening 138 receives a set screw 140 to mount the cross-member platform 116, 118 to the vertical support poles. Likewise, loosening of the set screws 140 allows for vertical repositioning of one or all of the cross-member platforms 116, 118.

The second exemplary I.V. stand 110 also includes an I.V. bag loop 125 and a standard equipment clamp 122. In exemplary form, the stand 110 is operative to support more than twelve syringe pumps 142, an infusion pump (not shown), and a monitor (not shown), as well a numerous bags of I.V. fluid (not shown).

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A portable intravenous stand comprising:
   a base including a plurality of wheels;
   a plurality of vertical supports extending from the base;
   a plurality of cross-members mounted to the plurality of vertical supports to maintain the vertical supports in relative position to one another, at least two of the plurality of cross-members each including a cable passageway opening and are vertically repositionable with respect to the plurality of vertical supports;
   an intravenous retainer loop mounted to at least one of the plurality of vertical supports; and
   a weight dowel proximate a central vertical axis of the portable intravenous stand and at least partially bounded by the plurality of vertical supports, the weight dowel adapted to receive a supplemental weight removably mounted thereto.

2. The portable intravenous stand of claim 1, wherein the plurality of vertical supports are equidistantly distributed about a vertical axis extending through the base and with respect to each other.

3. The portable intravenous stand of claim 1, wherein:
   the base includes at least three symmetrical legs; and
   at least three of the symmetrical legs each include at least one of the plurality of wheels.

4. The portable intravenous stand of claim 1, further comprising a handle mounted to at least one of a vertical support of the plurality of vertical supports and a cross-member of the plurality of cross-members.

5. The portable intravenous stand of claim 1, further comprising a plurality of intravenous retainer loops mounted to at least one of the plurality of vertical supports and the plurality of cross-members.

6. The portable intravenous stand of claim 1, further comprising a plurality of clamps vertically repositionable along at least one of the plurality of vertical supports.

7. The portable intravenous stand of claim 1, wherein at least one of the plurality of supports is circular in cross-section.

8. A portable intravenous stand comprising:
   a portable base with wheels;
   a plurality of vertical supports equidistantly spaced from one another and mounted to the portable base, the plurality of vertical supports including at least three supports triangularly oriented;
   a plurality of platforms mounted to the plurality of vertical supports, at least one of the plurality of platforms mounted to the at least three supports to maintain the at least three supports in a triangular orientation, where the at least one platform includes a cable passageway opening;
   an intravenous retainer loop mounted to at least one of the plurality of vertical supports; and
   a weight dowel proximate a central vertical axis of the portable intravenous stand and at least partially bounded by the plurality of vertical supports, the weight dowel adapted to receive a supplemental weight removably mounted thereto.

9. The portable intravenous stand of claim 8, wherein the at least one platform mounted to the at least three supports is vertically repositionable.

10. The portable intravenous stand of claim 8, further comprising a handle mounted to at least one of a vertical support of the plurality of vertical supports and a platform of the plurality of platforms.

11. The portable intravenous stand of claim 8, further comprising a plurality of intravenous retainer loops mounted to at least one of a vertical support of the plurality of vertical supports and a platform of the plurality of platforms.

12. The portable intravenous stand of claim 8, wherein:
   the portable base includes at least three symmetrical legs; and
   at least three of the symmetrical legs each include a wheel.

13. A portable intravenous stand comprising:
   a portable base;
   a plurality of peripheral vertical supports mounted to the portable base, the plurality of peripheral vertical supports including at least three supports triangularly oriented and generally equidistant from one another;
   a plurality of platforms repositionably mounted to the plurality of vertical supports, at least two of the plurality of platforms mounted to the at least three supports to maintain the at least three supports in a triangular orientation, at least one of the plurality of platforms includes a cable passageway opening;
   an intravenous loop mounted to at least one of: (a) the plurality of platforms; and (b) the plurality of vertical supports;
   a plurality of repositionable clamps vertically repositionable along at least one of the plurality of vertical supports; and
   a weight dowel proximate a central vertical axis of the portable intravenous stand and at least partially bounded by the plurality of peripheral vertical supports, the weight dowel adapted to receive a supplemental weight removably mounted thereto
   wherein the portable base is disproportionately weighted to lower a center of gravity of the stand.

* * * * *